(12) United States Patent
Fouilliart et al.

(10) Patent No.: US 12,240,795 B2
(45) Date of Patent: Mar. 4, 2025

(54) RHEOLOGICAL ADDITIVE BASED ON OPTIONALLY BIOSOURCED 1,5-PENTAMETHYLENEDIAMINE

(71) Applicant: Arkema France, Colombes (FR)

(72) Inventors: Carine Fouilliart, Verneuil en Halatte (FR); Virginie Ducastel, Verneuil en Halatte (FR); Vincent Leroy, Verneuil en Halatte (FR); Dmitri Colesnic, Verneuil en Halatte (FR)

(73) Assignee: Arkema France, Colombes (FR)

( * ) Notice: Subject to any disclaimer, the term of this patent is extended or adjusted under 35 U.S.C. 154(b) by 946 days.

(21) Appl. No.: 17/288,100

(22) PCT Filed: Oct. 18, 2019

(86) PCT No.: PCT/FR2019/052478
§ 371 (c)(1),
(2) Date: Apr. 23, 2021

(87) PCT Pub. No.: WO2020/084231
PCT Pub. Date: Apr. 30, 2020

(65) Prior Publication Data
US 2021/0380527 A1 Dec. 9, 2021

(30) Foreign Application Priority Data
Oct. 26, 2018 (FR) ..................... 18.59908

(51) Int. Cl.
C07C 235/10 (2006.01)
C08K 5/20 (2006.01)
C09D 7/43 (2018.01)

(52) U.S. Cl.
CPC .............. *C07C 235/10* (2013.01); *C08K 5/20* (2013.01); *C09D 7/43* (2018.01)

(58) Field of Classification Search
CPC ............ C07C 235/10; C09D 7/43; C08D 5/20
See application file for complete search history.

(56) References Cited

U.S. PATENT DOCUMENTS

| 3,977,894 A | * | 8/1976 | White | C09D 5/04 |
| | | | | 106/272 |
| 10,029,978 B2 | | 7/2018 | Bernard | |
| 2015/0274644 A1 | | 10/2015 | Bernard et al. | |
| 2018/0223076 A1 | | 8/2018 | Bernard et al. | |

OTHER PUBLICATIONS

Langmuir 2009, 25(15), 8392-8394, van Esch, J.H.
Weichao Ma et al. "Advances in Cadaverine Bacterial Production and Its Applications",, Engineering, vol. 3, No. 3, Jun. 1, 2017 (Jun. 1, 2017) pp. 308-317.

* cited by examiner

*Primary Examiner* — Yate' K Cutliff
(74) *Attorney, Agent, or Firm* — Debodhonyaa Sengupta

(57) ABSTRACT

The present invention relates to a rheology additive, according to which A) said additive consists of: a) at least one symmetrical fatty diamide of formula (I): (AGH)-CONH-(PMDA)-NHCO-(AGH) (I) with: (AGH): hydroxylated fatty acid residue R1CO2H, without —CO2H group, with R1 of C18 to C20 comprising a hydroxyl group, —NHCO— or —CONH—: amide group, —(PMDA): residue without amine groups of 1,5-pentamethylenediamine; or alternatively according to which: B) said additive comprises: a) at least one symmetrical fatty diamide as defined above according to formula (I) and, in addition, b) at least one other symmetrical fatty diamide of formula (II): (AGH)-CONH-(R)-NHCO-(AGH) (II) with (AGH), —NHCO— and —CONH— having the same definition as that above in said formula (I), and (R) being the residue without amine groups of a diamine, other than (PMDA), chosen from a cycloaliphatic, aliphatic or aromatic diamine.

20 Claims, No Drawings

RHEOLOGICAL ADDITIVE BASED ON OPTIONALLY BIOSOURCED 1,5-PENTAMETHYLENEDIAMINE

CROSS-REFERENCE TO RELATED APPLICATIONS

This application is a national stage application under 35 U.S.C. § 371 of PCT/FR2019/052478, filed Oct. 18, 2019 which claims benefit to application FR1859908, filed Oct. 26, 2018.

The present invention relates to a rheology additive based on a fatty diamide derived from 1,5-pentamethylenediamine, which is preferably biobased, more preferentially 100% biobased. It also relates to the uses thereof and more particularly as a rheology additive in binder compositions for applications in coatings, adhesive-bonding agents or adhesives, moulding compositions, mastics or leaktightness agents or cosmetics.

Methods for bacterial production of cadaverine as biobased diamine and the possible use thereof as a replacement for diamines of fossil origin for obtaining biobased polyamides with diacids are already described in *Engineering* 3 (2017), 308-317 These biobased polyamides are used as biobased thermoplastics.

Hexamethylenediamine is a diamine of fossil origin known to be used in rheology additives based on 12-hydroxystearic acid-based fatty diamides, as described for example in WO 2014/053774 and WO 2015/011375. However, the use of optionally biobased 1,5-pentamethylenediamine, such as cadaverine, to replace all or some of the hexamethylenediamine in the fatty diamides used as rheology additives does not appear to be known in the prior art.

The present invention proposes new fatty diamide rheology additives which are based on optionally biobased 1,5-pentamethylenediamine, such as cadaverine, as a partial or total replacement for a diamine from a fossil source, such as hexamethylenediamine, without affecting the rheological performance qualities and, on the contrary, while improving them compared with the 1,6-hexamethylenediamine-based diamide taken as reference, in particular in the presence of other organogelator agents with regard to sag resistance.

The rheological performance qualities of a fatty diamide are difficult to predict when replacing one component with another. Moreover, predicting the behaviour of a new organogelator agent still remains one of the major challenges of supramolecular chemistry, as described in *Langmuir* 2009, 25(15), 8392-8394. The physicochemical phenomena involved are very complex and difficult to predict, with the performance quality of the rheology additive governed by a sum of weak non-covalent interactions (hydrogen bonds, Van der Waals forces, etc.) according to the molecular structure of this additive. Furthermore, it is necessary to take into account the role of the solvent and the solvent-diamide interactions and to find a compromise between these interactions so that the diamide additive can be correctly activated (in gel form) and have the satisfactory rheological profile and also be stable with respect to storage. That proves to be a task that is not at all easy.

None of the prior art documents discloses or suggests the particular improvements observed with the diamides of the present invention.

The first subject of the present invention relates to an additive which, according to option A), consists of a) a symmetrical fatty diamide, which is preferably biobased, more preferentially 100% biobased, based on 1,5-pentamethylenediamine, preferably based on cadaverine, and a hydroxylated fatty acid, and, according to option B), it comprises said diamide a) and, in addition, b) a second symmetrical diamide based on a diamine other than 1,5-pentamethylenediamine, preferably other than cadaverine, and chosen from a cycloaliphatic, aliphatic or aromatic diamine, and a hydroxylated fatty acid.

The second subject of the invention relates to an organic binder composition which comprises at least one rheology additive as defined according to the invention.

The final subject of the invention relates to the use of said additive according to the invention in coating compositions, adhesive-bonding agent or adhesive compositions, moulding compositions, in particular composite, mastic or leaktightness agent compositions or cosmetic compositions.

The first subject of the invention thus relates to a rheology additive, according to which:

A) said additive consists of:
   a) at least one symmetrical fatty diamide, which is preferably biobased, more preferentially 100% biobased, of formula (I) below:

$$(AGH)\text{-}CONH\text{-}PMDA\text{-}NHCO\text{-}(AGH) \qquad (I)$$

with:
   (AGH): hydroxylated fatty acid residue $R_1CO_2H$, without —$CO_2H$ group, with $R_1$ of $C_{18}$ to $C_{20}$ comprising a hydroxyl group,
   NHCO— or —CONH—: amide group
   (PMDA): residue without amine groups of 1,5-pentamethylenediamine, preferably of cadaverine which is the biobased diamine 1,5-pentamethylenediamine or alternatively according to which:

B) said additive comprises:
   a) at least one symmetrical fatty diamide as defined above according to formula (I) and, in addition,
   b) at least one other symmetrical fatty diamide of formula (II) below:

$$(AGH)\text{-}CONH\text{-}(R)\text{-}NHCO\text{-}(AGH) \qquad (II)$$

with:
   (AGH), NHCO and CONN having the same definition as that given above in formula (I) and
   (R) being the residue without amine groups of a diamine other than 1,5-pentamethylenediamine, preferably other than cadaverine, chosen from a cycloaliphatic, aliphatic or aromatic diamine, preferably of a cycloaliphatic or linear aliphatic diamine, more preferentially of a cycloaliphatic diamine.

According to one particular option, said additive according to the invention is defined according to option A). This means that said additive contains 100% of fatty diamide a), preferably with a) being biobased, more preferentially with a) being 100% biobased, and thus contains 0% of diamide b) as defined above.

According to the present invention, the term "biobased" means based on raw materials of biological origin with renewable resources. These raw materials can be characterized and distinguished from non-renewable materials of fossil origin by the carbon 14 ($^{14}C$) content. Raw materials derived from renewable resources (100% biobased) have a $^{14}C$ content close to that of the atmosphere, whereas those of fossil origin (0% biobased) have a virtually zero content relative to materials of renewable origin. Quantitative determination of $^{14}C$ thus makes it possible to also determine the content of biobased raw material in the final product. For such an analysis, the product or raw material is burnt and the analysis is carried out on the $CO_2$ recovered according to the ASTM D-6866 method.

According to another particular option, said additive according to the invention is defined according to the alternative option B). This means that said fatty diamide b) is present with said diamide a) in said additive according to the invention. In such a case therefore, said additive of the invention is a mixture of diamide a), which is preferably biobased, more preferentially 100% biobased, and of fatty diamide b) as defined above. In said additive according to B), said fatty diamide a) is in particular present at a content by weight, relative to a)+b), ranging from 0.5 to 99.5%, preferably from 5 to 75%, more preferentially from 7 to 50%, even more preferentially from 10 to 45%.

Alternatively in said additive according to B), said fatty diamide a) is in particular present at a content by weight, relative to a)+b), ranging from 0.5 to 99.5% or 1 to 95% or 5 to 75% or 5 to 50% or 5 to 45% or 7 to 50% or 7 to 45% or 10 to 50% or 10 to 45%, or 50 to 95% or 55 to 95% or 60 to 95% or 70 to 95% or 50 to 90% or 55 to 90% or 60 to 90% or 70 to 90% or 30 to 70% or 35 to 65% or 40 to 60% or 45 to 55%, it being possible for the upper and lower limits of the ranges indicated to be combined with one another.

Contrary to the diamides based on 1,6-hexamethylenediamine, the biobased fatty diamide a) has the advantage of providing excellent synergy and compatibility in the presence of the second fatty diamide b) so as to make it possible to adjust the applicative performance qualities according to the working application.

The hydroxylated fatty acid $R_1CO_2H$ can be selected from: 12-hydroxystearic acid (12HSA), 9-hydroxystearic acid, 10-hydroxystearic acid or 14-hydroxyeicosanoic acid, or mixtures thereof, preferably binary mixtures. The hydroxylated fatty acid $R_1CO_2H$ is preferably 12-hydroxystearic acid (12HSA).

Regarding the diamine $H_2N-R-NH_2$ on which the second fatty diamide b) is based, when the latter is present in the rheology additive according to the invention, it may be cycloaliphatic, linear aliphatic or aromatic, preferably cycloaliphatic or linear aliphatic, more preferentially cycloaliphatic.

As suitable examples of cycloaliphatic primary diamines (cycloaliphatic meaning comprising in its structure at least one saturated $C_6$ ring), mention may be made of 1,3- or 1,4-diaminocyclohexane, 1,3- or 1,4-bis(aminomethyl)cyclohexane and isophorone diamine.

According to one particular option of the rheology additive according to the invention, the residue (R) of the fatty diamide b) is the residue of 1,3-bis(aminomethyl)cyclohexane. In this embodiment, the content by weight of the fatty diamide a), relative to the weight a)+b), can in particular range from 5 to 50% or 5 to 45% or 7 to 50% or 7 to 45% or 10 to 50% or 10 to 45%, or 50 to 95% or 55 to 95% or 60 to 95% or 70 to 95% or 50 to 90% or 55 to 90% or 60 to 90% or 70 to 90%, it being possible for the upper and lower limits of the ranges indicated to be combined with one another.

As suitable examples of linear aliphatic primary diamines, mention may be made of the primary diamines ethylenediamine, diethylenetriamine, 1,3-propylenediamine, 1,4-butylenediamine, 1,6-hexamethylenediamine.

According to one particular option of the rheology additive according to the invention, the residue (R) of the fatty diamide b) is the residue of 1,6-hexamethylenediamine. In this embodiment, the content by weight of the fatty diamide a), relative to the weight a)+b), can in particular range from 30 to 70% or 35 to 65% or 40 to 60% or 45 to 55%, it being possible for the upper and lower limits of the ranges indicated to be combined with one another.

As suitable examples of aromatic diamines (aromatic meaning comprising in its structure at least one aromatic ring), mention may be made of: o-, m- and p-phenylenediamine, o-, m- and p-xylylenediamine, preferably m-xylylenediamine.

The preparation of the fatty diamides a) and b) is carried out according to synthesis processes well known to those skilled in the art, by reacting the hydroxylated fatty acid with the diamine or the diamine mixture in the molten state at a temperature between 135 and 180° C. with elimination of the condensation water. The amine/carboxy equivalents ratio is in a range around the stoichiometry (0.95/1.05). The reaction is considered to be finished when the amine number or the acid number is less than 8, preferably less than 5 mg KOH/g. The final molten fatty diamide is cooled and then ground in a micronizer and formed into micronized powder before final use.

More particularly, the rheology additive according to the invention is in the form of a micronized powder which has a particle size corresponding to a volume mean size ranging from 1 to 15 μm, measured by dry particle size analysis. The particle size analysis was determined in accordance with Standard ISO 13320:2009 using the Malvern Mastersizer S instrument. This technique is based on the principle that particles passing through a laser beam diffract light according to a different angle depending on their size: small particles diffract at large angles, whereas particles of greater sizes diffract at small angles.

The second subject of the present invention relates to an organic binder composition which comprises at least one rheology additive as defined above.

More particularly, said organic binder composition is a coating composition, adhesive-bonding agent or adhesive composition, moulding composition, in particular composite, mastic or leaktightness agent composition or cosmetic composition.

More particularly, the coating compositions are chosen from paints, varnishes and inks in a non-reactive solvent medium and gel coats in a reactive solvent medium.

Said organic binder may be selected from: epoxy resins, unsaturated and saturated polyesters, vinyl esters, alkyds, silanized (or silylated) resins, polyurethanes, polyester amides, solvented acrylic resins, multifunctional acrylic monomers and/or oligomers or acrylated acrylic resins with reactive diluent or inert resins diluted in a reactive or non-reactive solvent.

More particularly, in the case of crosslinkable compositions of adhesives or leaktightness agents, said binder may comprise silylated polyurethanes, silylated polyethers and polyesters, silylated polybutadienes.

Another subject of the invention relates to the use of the rheology additive as defined according to the invention in coating compositions, adhesive-bonding agent or adhesive compositions, moulding compositions, in particular composite, mastic or leaktightness agent compositions or cosmetic compositions.

Finally, also part of the invention is a finished product chosen from a coating film, an adhesive-bonding agent seal, an adhesive seal, a mastic seal, a leaktightness agent seal, a cosmetic product or a moulded part, in particular a composite part, which finished product results from the use of at least one rheology additive as defined above according to the present invention.

The following examples are given by way of illustration of the present invention and of its performance qualities and in no way limit the invention which is defined by the scope of the claims.

EXPERIMENTAL PART

1) Raw Materials

See Table 1 below

TABLE 1 raw materials used in synthesis and in formulation

| Product | Function | Product reference | Supplier |
|---|---|---|---|
| 12-hydroxystearic acid | Hydroxy fatty acid | 12HSA | Jayant Agro |
| 1,6-hexamethylenediamine (HMDA) | Diamine | HMDA | Solvay |
| 1,5-pentamethylenediamine (PMDA) | Diamine | Cadaverine | Sigma Aldrich |
| 1,3-bis(aminomethyl)cyclo-hexane (1.3BAC) | Diamine | 1,3-BAC | Mitsubishi Chemicals |
| Araldite ® GZ 7071 X75 | Binder | Araldite ® GZ 7071 X75 | Hunstman |
| Araldite ® GY 783 BD | Binder | Araldite ® GY 783 BD | Hunstman |
| BYK ® A-530 | Antifoam/Defoamer | | BYK Additives |
| Disperbyk ® 110 | Wetting agent | | BYK Additives |
| Titanium dioxide | Pigment | TIONA ® 595 | Cristal |
| Zinc Phosphate | Anti-corrosion pigment | ZP10 | Heubach |
| Finntalc | Filler | MO5 | Mondo minerals |
| Silica | Filler | C-400 | Sibelco |
| Butanol | Solvent | Butanol | VWR |

2) Synthesis/Preparation of the Additives Tested

Each additive is prepared according to the procedure described below.

Example 1: Diamide According to Definition a) of the Invention: 12-HSA-PMDA-12-HSA 69.75 g of 1,5-pentamethylenediamine (0.68 mol, 1 eq) and 430.25 g of 12-hydroxystearic acid (1.36 mol, 2 eq) are added to a 1 litre round-bottomed flask equipped with a thermometer, a Dean-Stark apparatus, a condenser and a stirrer. The mixture is heated to 180° C. under an inert atmosphere. The water removed accumulates in the Dean-Stark apparatus from 150° C. The reaction is monitored by the acid number and the amine number. When the acid and amine numbers are respectively less than 5, the reaction is halted. The reaction mixture is cooled to 140° C. and is discharged into a silicone mould. Once cooled to ambient temperature, the product is converted into flakes.

Example 2: Diamide According to the Prior Art: 12-HSA-1.3BAC-12HSA 92.04 g of 1,3-bis(aminomethyl)cyclohexane (0.65 mol, 1 eq) and 407.96 g of 12-hydroxystearic acid (1.30 mol, 2 eq) are added to a 1 litre round-bottomed flask equipped with a thermometer, a Dean-Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 5, the reaction is halted. The reaction mixture is cooled to 140° C. and is discharged into a silicone mould. Once cooled to ambient temperature, the product is converted into flakes.

Example 3: Diamide According to the Prior Art: 12-HSA-HMDA-12-HSA 77.83 g of 1,6-hexamethylenediamine (0.67 mol, 1 eq) and 422.17 g of 12-hydroxystearic acid (1.34 mol, 2 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 5, the reaction is halted. The reaction mixture is cooled to 140° C. and is discharged into a silicone mould. Once cooled to ambient temperature, the product is converted into flakes.

Example 4: Mixture a)+b) According to the Invention with Diamide of Example 1 (Diamide According to a))+Diamide of Example 2 (Diamide According to b))

6.64 g of 1,5-pentamethylenediamine (0.065 mol, 0.1 eq), 83.26 g of 1,3-bis(aminomethyl)cyclohexane (0.585 mol, 0.9 eq) and 410.10 g of 12-hydroxystearic acid (1.3 mol, 2 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 5, the reaction is halted. The reaction mixture is cooled to 140° C. and is discharged into a silicone mould. Once cooled to ambient temperature, the product is converted into flakes.

Example 5: Comparative Mixture According to the Prior Art: Diamide of Example 2+Diamide of Example 3

7.55 g of 1,6-hexamethylenediamine (0.065 mol, 0.1 eq), 83.11 g of 1,3-bis(aminomethyl)cyclohexane (0.585 mol, 0.9 eq) and 409.34 g of 12-hydroxystearic acid (1.3 mol, 2 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 5, the reaction is halted. The reaction mixture is cooled to 140° C. and is discharged into a silicone mould. Once cooled to ambient temperature, the product is converted into flakes.

Example 6: Mixture According to the Invention: Diamide of Example 1+Diamide of Example 3

39.63 g of 1,6-hexamethylenediamine (0.34 mol, 0.5 eq), 34.85 g of 1,5-pentamethylenediamine (0.34 mol, 0.5 eq) and 425.22 g of 12-hydroxystearic acid (1.36 mol, 2 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 5, the reaction is halted. The reaction mixture is cooled to 140° C. and is discharged into a silicone mould. Once cooled to ambient temperature, the product is converted into flakes.

Example 7: Mixture According to the Invention: Diamide of Example 1+Diamide of Example 3

Example 4 is reproduced, introducing 55.69 g of 1,5-pentamethylenediamine (0.54 mol, 0.8 eq), 19.37 g of 1,3-bis(aminomethyl)cyclohexane (0.14 mol, 0.2 eq) and 424.64 g of 12-hydroxystearic acid (1.36 mol, 2 eq).

Example 8: Comparative Mixture According to the Prior Art: Diamide of Example 2+Diamide of Example 3

Example 5 is reproduced, introducing 62.38 g of 1,6-hexamethylenediamine (0.54 mol, 0.8 eq), 19.08 g of 1,3-bis(aminomethyl)cyclohexane (0.13 mol, 0.2 eq) and 418.25 g of 12-hydroxystearic acid (1.34 mol, 2 eq).

3) Preparation of the Paint Formulas

The amides prepared were evaluated in formulations of epoxy paints at a high solids content (or high dry extract) in xylene.
A "millbase" formulation is prepared with the proportions presented in Table 2 below and in the following way:
The following and successive operations are carried out in a disperser bowl (Dispermill® 2075 yellow line, supplier: Erichsen) heated by a jacket system:
   Introduction of the epoxy binders and also the dispersant and the defoamer. The homogenization takes place for 2 minutes at 800 revolutions/minute (800 revolutions per minute or 800 rpm).
   Introduction of the fillers and pigments, then milling at 3000 rpm for 30 minutes using a 7 cm blade. The jacketed bowl allows this step to take place at ambient temperature with a bath of cold water (at 20° C.).
   Introduction of the solvents (butanol according to Table 2) and homogenization.

TABLE 2

| part A "millbase" | | |
|---|---|---|
| A - "Millbase" composition | Function | weight % |
| Araldite ® GZ 7071 X75 | Binder | 17.3 |
| Araldite ® GY 783 BD | Binder | 12.9 |
| BYK ® A-530 | Antifoam/Defoamer | 0.5 |
| Disperbyk ® 110 | Wetting agent | 0.5 |
| Tiona ® 595 | Pigment | 6.0 |
| Zinc Phosphate ZP10 | Anti-corrosion pigment | 7.5 |
| Finntalc MO5 | Filler | 9.4 |
| Silice C-400 | Filler | 19.0 |
| Butanol | Solvent | 5.4 |
| Rheology additive | Additive | 0.8 |

The evaluation of the rheological performance qualities requires the addition of a part B which is the curing agent according to the formula presented in Table 3.

TABLE 3

| part B curing agent | | |
|---|---|---|
| B - Curing agent | Function | weight % |
| Crayamid ® 140 | Curing agent | 8.8 |
| Xylene | Solvent | 11.9 |

4) Activation of the Additive 24 hours after the preparation of the millbase, the formulation is again dispersed at 3000 rpm using a 4 cm blade. The diamide to be evaluated is introduced into the millbase and activated in situ at 55° C. for 20 minutes and at 3000 rpm.
The evaluation is carried out only 24 hours after the activation and 30 minutes after the addition to the millbase of the curing agent diluted in xylene (see Table 3) and the paints thus obtained are adjusted in terms of paint-application viscosity with a xylene/butanol mixture (1/1 by weight) at approximately 0.4 P or approximately 400 mPa·s (more specifically at 0.37-0.38 P or 370-380 mPa·s) measured on the cone 4 at 25° C. at 2500 $s^{-1}$ using a Brookfield® CAP 1000 viscometer. The proportions between the curing agent and the mixture of 10 solvents are defined in Table 4 below. The amount of 1/1 xylene/butanol mixture used for the viscosity adjustment can vary, but in general by less than 1% from one test to the other. After the adjustment, the paint is mixed/homogenized at 1500 rpm for 25 minutes, then left to stand for 30 minutes before the evaluation 24 hours later.

5) Results

TABLE 4

| Sag resistance results | | |
|---|---|---|
| Example | Additives | Sag resistance (μm) |
| 1 | 12HSA-PMDA-12HSA | 325 |
| 3 (Comp) | 12HSA-HMDA-12HSA | 325 |
| 2 (Comp) | 12HSA-1.3BAC-12HSA | 500 |
| 5 | 12HSA-1.3BAC-12HSA (90 mol %) 12HSA-PMDA-12HSA (10 mol %) | 650 |
| 4 (Comp) | 12HSA-1.3BAC-12HSA (90 mol %) 12HSA-HMDA-12HSA (10 mol %) | 500 |
| 6 | 12HSA-PMDA-12HSA (50 mol %) 12HSA-HMDA-12HSA (50 mol %) | 450 |
| 7 | 12HSA-1.3BAC-12HSA (20 mol %) 12HSA-PMDA-12HSA (80 mol %) | 525 |
| 8 (Comp) | 12HSA-1.3BAC-12HSA (20 mol %) 12HSA-HMDA-12HSA (80 mol %) | 500 |

TABLE 5

| Rheological results | | | | |
|---|---|---|---|---|
| | Brookfield viscosity at 25° C. (mPa · s) | | | |
| Example | 1 rpm | 5 rpm | 10 rpm | 50 rpm |
| 1 | 10 000 | 3760 | 2600 | 1312 |
| 2 | 13 600 | 4640 | 2990 | 1400 |
| 3 | 9800 | 3520 | 2400 | 1112 |
| 4 | 15 400 | 4880 | 3140 | 1408 |
| 5 | 19 000 | 5920 | 3780 | 1608 |
| 6 | 12 400 | 4240 | 2840 | 1320 |
| 7 | 14 800 | 4880 | 3240 | 1440 |
| 8 | 14 400 | 4640 | 3080 | 1384 |

6) Conclusion

The results of the sag resistance test clearly show that the diamide of Example 1 based on PMDA exhibits performance qualities that are at least equal to the diamide of Example 3 based on HMDA. Thus, it can be concluded that it is entirely possible to completely replace the diamine 1,6-hexamethylenediamine with 1,5-pentamethylenediamine, preferably with a biobased amine which is cadaverine, without impairing the rheological performance qualities in the system studied.

Moreover, the mixture of the diamide of Example 1 based on PMDA and of the diamide of Example 3 based on HMDA shows positive synergy in the sag resistance test in comparison with each diamide taken individually (cf. comparison of Examples 1 and 3 with respect to Example 6). Thus, it can be concluded that the partial replacement of 1,6-hexamethylenediamine with 1,5-pentamethylenediamine improves the rheological performance qualities in the system studied.

Furthermore, the mixture of the diamide of Example 1 based on PMDA with another diamide, for example the diamide of Example 2 based on 1.3BAC, shows positive synergy in the sag resistance test in comparison with a comparative mixture comprising the diamide of Example 3 based on HMDA, in the same proportions (cf. comparison of Example 5 according to the invention with Comparative Example 4 or comparison of Example 7 according to the invention with Comparative Example 8).

The use of an additive based on 1,5-pentamethylenediamine, which is preferably biobased, makes it possible not only to meet an environmental challenge, but also to contribute to the obtaining of excellent rheological performance qualities, in particular in paint formulations with a high dry extract.

The invention claimed is:

1. A rheology additive wherein:
said additive comprises:
a) at least one symmetrical fatty acid diamide of formula (I):

(AGH)-CONH-(PMDA)-NHCO-(AGH)  (I), and, in addition,
b) at least one other symmetrical fatty diamide of formula (II):

(AGH)-CONH-(R)-NHCO-(AGH)  (II)

wherein:
(AGH) is a residue of a hydroxylated fatty acid $R_1CO_2H$, without —$CO_2H$ group, wherein the hydroxylated fatty acid $R_1CO_2H$ is selected from the group consisting of: 12-hydroxystearic acid (12HSA), 9-hydroxystearic acid, 10-hydroxystearic acid and 14-hydroxyeicosanoic acid,
—NHCO— and —CONH— is each an amide group,
(PMDA) is a residue without amine groups of 1,5-pentamethylenediamine, and
(R) is a residue without amine groups of a diamine, other than (PMDA), chosen from the group consisting of a cycloaliphatic, linear aliphatic and aromatic diamine.

2. The rheology additive according to claim 1, wherein said fatty diamide a) is present at a content by weight, relative to a)+b), ranging from 0.5 to 99.5%.

3. The rheology additive according to claim 1, wherein said fatty diamide a) is present at a content by weight, relative to a)+b), ranging from 0.5 to 99.5% or 1 to 95% or 5 to 75% or 5 to 50% or 5 to 45% or 7 to 50% or 7 to 45% or 10% to 50% or 10% to 45% or 50 to 95% or 60 to 95% or 70 to 95% or 50 to 90% or 55 to 90% or 60 to 90% or 70 to 90% or 30 to 70% or 35 to 65% or 40 to 60% or 45 to 55%.

4. The rheology additive according to claim 1, wherein (R) is the residue of a cycloaliphatic diamine chosen from 1,3- or 1,4-diaminecyclohexane, 1,3- or 1,4-bis(aminomethyl)cyclohexane and isophorone diamine.

5. The rheology additive according to claim 1, wherein (R) is a residue of 1,3-bis(aminomethyl)cyclohexane.

6. The rheology additive according to claim 1 in the form of a micronized powder with a particle size corresponding to a volume mean size ranging from 1 to 15 μm.

7. The rheology additive according to claim 4, wherein the content by weight of the fatty diamide a), relative to the weight a)+b), is from 5 to 50% or 5 to 45% or 7 to 50% or 7 to 45% or 10 to 50% or 10 to 45% or 50 to 95% or 55 to 95% or 60 to 95% or 70 to 95% or 50 to 90% or 55 to 90% or 60 to 90% or 70 to 90%.

8. The rheology additive according to claim 1, wherein (R) is the residue of a linear aliphatic diamine chosen from ethylenediamine, diethylenetriamine, 1,3-propylenediamine, 1,4-butylenediamine, and 1,6-hexamethylenediamine.

9. The rheology additive according to claim 8, wherein (R) is the residue of 1,6-hexamethylenediamine.

10. The rheology additive according to claim 8, wherein the content by weight of the fatty diamine a), relative to the weight a)+b), ranges from 30 to 70% or 35 to 65% or 40 to 60% or 45 to 55%.

11. The rheology additive according to claim 1, wherein (R) is the residue of an aromatic diamine chosen from o-, m- and p-phenylenediamine or o-, m- and p-xylenediamine.

12. An organic binder composition, comprising at least one rheology additive as defined according to claim 1.

13. The organic binder composition according to claim 12, wherein said organic binder composition is a coating composition, adhesive-bonding agent or adhesive composition, moulding composition, composite, mastic or leaktightness agent composition or cosmetic composition.

14. The organic binder composition according to claim 12, wherein said organic binder is selected from: epoxy resins, unsaturated and saturated polyesters, vinyl ester, alkyds, silanized resins, polyurethanes, polyester amides, solvented acrylic resins, multifunctional acrylic monomers and/or oligomers, and acrylated acrylic resins with reactive diluent or inert resins diluted in a reactive or non-reactive solvent.

15. The rheology additive according to claim 2, wherein said fatty diamide a) is present at a content by weight, relative to a)+b), ranging from 5 to 75%.

16. The rheology additive according to claim 15, wherein said fatty diamide a) is present at a content by weight, relative to a)+b), ranging from 7 to 45%.

17. The rheology additive according to claim 4, wherein the content by weight of the fatty diamide a), relative to the weight a)+b), is from 5 to 50%.

18. The rheology additive according to claim 4, wherein the content by weight of the fatty diamide a), relative to the weight a)+b), is from 50 to 95%.

19. The rheology additive according to claim 8, wherein the content by weight of the fatty diamine a), relative to the weight a)+b), ranges from 30 to 70%.

20. The rheology additive according to claim 19, wherein the content by weight of the fatty diamine a), relative to the weight a)+b), ranges from 40 to 60%.

* * * * *